(12) United States Patent
Lee et al.

(10) Patent No.: US 10,166,173 B2
(45) Date of Patent: Jan. 1, 2019

(54) POLYURETHANE MICROPARTICLES COATED WITH A ZINC SALT AND METHODS FOR THE PREPARATION THEREOF

(71) Applicants: Dow Global Technologies LLC, Midland, MI (US); Rohm and Haas Company, Philadelphia, PA (US)

(72) Inventors: Wai Kin Lee, Singapore (SG); Wei Lu, Shanghai (CN); Wuye Ouyang, Shanghai (CN); Xiao Yi Pang, Shanghai (CN); Tong Sun, Shanghai (CN); Xianda Xiao, Shanghai (CN); Shiling Zhang, Shanghai (CN)

(73) Assignees: Dow Global Technologies LLC, Midland, MI (US); Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 15/532,141

(22) PCT Filed: Dec. 2, 2014

(86) PCT No.: PCT/CN2014/092734
§ 371 (c)(1),
(2) Date: Jun. 1, 2017

(87) PCT Pub. No.: WO2016/086348
PCT Pub. Date: Jun. 9, 2016

(65) Prior Publication Data
US 2017/0266083 A1  Sep. 21, 2017

(51) Int. Cl.
| | |
|---|---|
| *A61K 8/02* | (2006.01) |
| *A61K 8/27* | (2006.01) |
| *A61K 8/49* | (2006.01) |
| *A61K 8/87* | (2006.01) |
| *A61Q 5/00* | (2006.01) |
| *A61Q 5/02* | (2006.01) |

(52) U.S. Cl.
CPC .............. *A61K 8/0241* (2013.01); *A61K 8/27* (2013.01); *A61K 8/4933* (2013.01); *A61K 8/87* (2013.01); *A61Q 5/006* (2013.01); *A61Q 5/02* (2013.01); *A61K 2800/412* (2013.01); *A61K 2800/436* (2013.01); *A61K 2800/58* (2013.01); *A61K 2800/621* (2013.01); *A61K 2800/651* (2013.01); *A61K 2800/652* (2013.01); *A61K 2800/654* (2013.01)

(58) Field of Classification Search
None
See application file for complete search history.

(56) References Cited

U.S. PATENT DOCUMENTS

| | | | |
|---|---|---|---|
| 2002/0034486 A1* | 3/2002 | Midha | A61K 8/0245 424/70.2 |
| 2006/0251688 A1 | 11/2006 | Gajanan et al. | |
| 2007/0053950 A1 | 3/2007 | Gajanan et al. | |
| 2008/0206355 A1* | 8/2008 | Schwartz | A61K 8/27 424/604 |
| 2010/0196506 A1 | 8/2010 | Gruzins et al. | |
| 2013/0296289 A1 | 11/2013 | Hall et al. | |
| 2014/0271757 A1* | 9/2014 | Agrawal | A61K 33/34 424/405 |

FOREIGN PATENT DOCUMENTS

WO    2010039145 A1    4/2010

* cited by examiner

*Primary Examiner* — Susan T Tran
*Assistant Examiner* — William Craigo
(74) *Attorney, Agent, or Firm* — Edward L. Brant

(57) ABSTRACT

Provided are compositions and methods that are useful for hair care compositions. The compositions comprise polyurethane microparticles coated with zinc salt particles, wherein the ratio of zinc salt to polyurethane is in a range of from 1:99 to 3:7, and the polyurethane microparticles have an average particle size of less than 100 microns. Also provided are methods of preparation of such compositions.

6 Claims, 3 Drawing Sheets

POLYURETHANE MICROPARTICLES COATED WITH A ZINC SALT AND METHODS FOR THE PREPARATION THEREOF

FIELD OF THE INVENTION

This invention relates generally to polyurethane microparticles coated with a zinc salt, their use in hair care compositions, and methods of preparation for the same.

BACKGROUND

Hair care products such as shampoos often contain active ingredients that prevent dandruff from forming. Dandruff is a condition manifested by shedding of dead skin cells from the scalp caused by yeast and fungus. Accordingly, anti-dandruff shampoos have included zinc salts, such as zinc pyrithione, which have antimicrobial activity. Zinc pyrithione particles, however, are known to agglomerate, which impedes their deposition and/or retention on the scalp. In a shampoo formulation, zinc pyrithione particles also disrupt the pearlescent appearance attributed to ethylene glycol di-stearate or mica-based pearlescent agents. Zinc pyrithione is also known to contribute to poor smoothness/sensory feel after deposition onto hair.

Different approaches have been taken to improve upon deposition performance of anti-dandruff zinc salts. For example, U.S. Patent Application Publication No. US 2013/0296289 discloses anti-dandruff shampoo formulations containing a zinc salt, branched alkyloyl isethionate, a fatty acyl isethionate and a co-surfactant. PCT International Publication No. WO 2010/039145 discloses hair care products containing zinc pyrithione in combination with a polymer selected from a powder blend of partially neutralized monobutyl ester of poly(methyl vinyl ether maleic acid) and polyvinyl pyrrolidone, an alkylated grafted vinyl pyrrolidone graft copolymer, and a linseed oil-modified dicarboxylic acid half-ester of maleic acid. The prior art suffers, however, from poor aesthetic properties such as an unpleasant visual appearance and a lack of smoothness after deposition on hair.

Consequently, there is a need to develop new additives for use in hair care formulations that provide good deposition of zinc salts while not disrupting the pleasing pearlescent appearance desired by consumers or leaving the hair with a lack of smoothness.

STATEMENT OF INVENTION

One aspect of the invention provides a composition comprising polyurethane microparticles coated with zinc salt particles, wherein the ratio of zinc salt to polyurethane is in a range of from 1:99 to 3:7, and the polyurethane microparticles have an average particle size of less than 100 microns.

In another aspect, the invention provides a personal care composition comprising (a) polyurethane microparticles coated with zinc salt particles, wherein the ratio of zinc salt to polyurethane is in a range of from 1:99 to 3:7, and the polyurethane microparticles have an average particle size of less than 100 microns, and (b) at least one cosmetically acceptable cationic polymer, emollient, surfactant, rheology modifier, or cosmetic active. In certain embodiments, the zinc salt comprises zinc pyrithione having an average particle size of less than 2 microns.

Another aspect of the invention provides a process for preparing a zinc pyrithione coated polyurethane microparticle comprising the steps of (a) reacting a pre-polymer reaction mixture comprising an isocyanate and a polyol to provide a polyurethane pre-polymer, (b) contacting the polyurethane pre-polymer with a polyvinyl alcohol and an amine to provide a polyurethane slurry, (c) mixing the polyurethane slurry with a zinc pyrithione suspension to provide a polyurethane/zinc pyrithione composite dilution, and (d) spray drying the polyurethane/zinc pyrithione composite dilution to provide a zinc pyrithione coated polyurethane microparticle.

In yet another aspect, the invention provides a method for reducing dandruff comprising applying to the scalp a hair care composition comprising (a) polyurethane microparticles coated with zinc salt particles, wherein the ratio of zinc pyrithione to polyurethane is in a range of from 1:99 to 3:7, and the polyurethane microparticles have an average particle size of less than 100 microns, and (b) at least one cosmetically acceptable cationic polymer, emollient, surfactant, rheology modifier, or cosmetic active.

DETAILED DESCRIPTION

Figure 1:
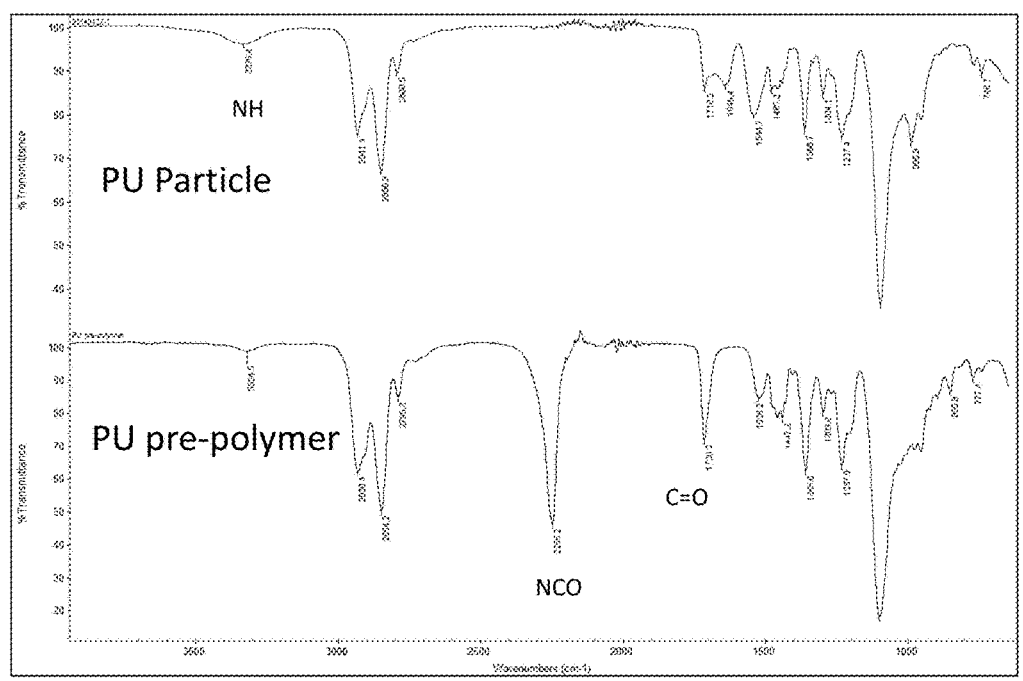
FIG. 1 shows the IR spectra of a polyurethane pre-polymer solution (below) and polymerized polyurethane microparticle (above).

The inventors have now surprisingly found that polyurethane microparticles coated with zinc salts provide superior deposition and/or retention when applied to the scalp, and maintain a pleasing visual appearance and a pleasant tactile feel when incorporated into shampoo formulations, while also leaving hair treated with such formulations feeling silky and smooth. Accordingly, the present invention provides in one aspect polyurethane microparticles coated with a zinc salt, wherein the ratio of zinc salt to polyurethane is in a range of from 1:99 to 3:7, and the polyurethane microparticles have an average particle size of less than 100 microns.

The polyurethane microparticles useful in the present invention may be formed by the combination of a polyol and an isocyanate and a catalyst promoting the reaction between the two components. Accordingly, one aspect of the present invention provides a process for preparing a polyurethane microparticle coated with a zinc salt comprising the steps of (a) mixing a pre-polymer reaction mixture comprising an isocyanate and a polyol to provide a polyurethane pre-polymer, (b) reacting the polyurethane pre-polymer in the presence of a catalyst and a polyvinyl alcohol to provide a polyurethane slurry containing polyurethane microparticles, (c) mixing the polyurethane slurry with a zinc salt suspension to provide a polyurethane/zinc salt composite dilution, and (d) spray drying the polyurethane/zinc salt composite dilution to provide a polyurethane microparticle coated with a zinc salt.

Isocyanates useful in the pre-polymer reaction mixture are those known in the art including an isocyanate functional group, i.e., —N═C═O. Suitable isocyanates include, for example, toluene diisocyanate, methylene diisocyanate, isophorone diisocyanate, cyclohexane-1,3-diisocyanate, cyclohexane-1,4-diisocyanate, hexamethylene diisocyanate, m-tetramethyloxylene diisocyanate, 2,2,4-trimethyl hexamethylene diioscyanate, 2,4,4-trimethyl hexamethylene diioscyanate, 2,5-norbornane diisocyanate, m-xylene diisocyanate, bis-(cyclohexyl isocyanate)methane, and combinations thereof. Preferably, the isocyanate comprises isophorone diisocyanate.

Polyols useful in the pre-polymer reaction mixture are those known in the art as useful in the production of polyurethanes. Suitable polyols include, for example, ethylene glycol, diethylene glycol, 1,4-butane diol, poly(tetramethylene ether glycol), polyoxypropylene glycol, polyether triol, and polyether tetrol. Preferably, the polyol comprises poly(tetramethylene ether glycol).

Catalysts useful in the reaction of the pre-polymer mixture are those known in the art as useful in the production of polyurethanes, including, for example, amine catalysts and organometallic catalysts. Suitable amine catalysts include, for example, ethylenediamine (EDA), triethylenetetramine (TETA), isophoronediamine (IDPA), diethylenetriamine (DETA), N,N-dimethylcyclohexylamine, N,N-dimethylcetylamine, diamino-bicyclooctane, and combinations thereof. Suitable organometallic include, for example, stannous octoate, dibutyltin dilaurate, and combinations thereof. Preferably, the catalyst comprises DETA.

In certain embodiments, the polyurethane microparticles in the polyurethane slurry have an average particle size of less than 100 microns, preferably less than 50 microns, more preferably less than 30 microns, and even more preferably less than 20 microns. In certain embodiments, the polyurethane microparticles have a particle size in the range of from 1 to 100 microns, preferably 5 to 50 microns, more preferably 5 to 30 microns, and even more preferably 5 to 20 microns.

The zinc salts useful in the present invention include those that are useful as anti-dandruff agents and can be in a powder form or a suspension. Suitable zinc salt suspensions include, for example, 10 to 80%, preferably 30 to 60%, zinc salt in water. Suitable zinc salts include, for example, zinc pyrithione, zinc sulfate and hydrates thereof (e.g., zinc sulfate hexahydrate), and combinations thereof. Preferably, the zinc salt is zinc pyrithione, which can be prepared by reacting 1-hydroxy-2-pyridinethione or a soluble salt thereof with a zinc salt, such as zinc sulfate, to form zinc 1-hydroxy-2-pyridinethione (an alternative name for zinc pyrithione). In certain embodiments, the zinc salt has an average particle size of less than 3 microns, preferably less than 2 microns, and more preferably less than 1 micron. In certain embodiments, the zinc salt has a particle size ranging from 0.02 to 2.0 microns, and preferably from 0.03 to 0.8 microns.

In certain embodiments, the polyurethane/zinc salt composite dilution contains the zinc salt and polyurethane microparticles in a weight ratio of from 1:99 to 3:7, preferably from 0.5:9.5 to 2.0:8.0, and more preferably from 1.0:9.0 to 2.0:8.0.

Spray drying methods for useful forming the zinc salt coated polyurethane microparticles are known in the art. Any known spray drying method can be used in the present invention. The resulting zinc salt coated polyurethane microparticles have, in certain embodiments, an average particle size of less than 100 microns, preferably less than 50 microns, and more preferably less than 30 microns. In certain embodiments, the zinc salt coated polyurethane microparticles have a particle size in the range of from 1 to 100 microns, preferably 1 to 50 microns, and more preferably 5 to 30 microns.

Another aspect of the present invention provides a hair care composition comprising the zinc salt coated polyurethane microparticles described above, and at least one cosmetically acceptable cationic polymer, emollient, surfactant, rheology modifier, or cosmetic active. In the present invention, "hair care" relates to personal care compositions to be topically applied to a person (i.e., not ingested), and in particular a person's hair. Examples of hair care compositions include, but are not limited to, shampoos, leave-on conditioners, styling gels, hairsprays, and mousses. In certain preferred embodiments, the hair care composition is a shampoo, preferably an anti-dandruff shampoo. Preferably, the hair care compositions are cosmetically acceptable. As used herein, "cosmetically acceptable" refers to ingredients typically used in personal care compositions, and is intended to underscore that materials that are toxic when present in the amounts typically found in personal care compositions are not contemplated as part of the present invention. The hair care compositions of the invention may be manufactured by processes well known in the art, for example, by means of conventional mixing, dissolving, granulating, emulsifying, encapsulating, entrapping, or lyophilizing processes.

A person of ordinary skill in the art can readily determine the effective amount of zinc salt coated polyurethane microparticles that should be used in a particular composition in order to provide the desired benefits described herein (e.g., an effective anti-dandruff agent) via a combination of general knowledge of the applicable field as well as routine experimentation where needed. By way of non-limiting example, the amount of zinc salt coated polyurethane microparticles in the hair care compositions of the invention may be in a range of from 0.1 to 10.0 weight %, preferably of from 0.5 to 5.0 weight %, and more preferably of from 1.0 to 3.0 weight %, based on the total weight of the composition.

In certain embodiments, the inventive hair care compositions include a cationic polymer. Suitable cationic polymers include, for example, polysaccharides modified to have a positive charge (e.g., cationic cellulose derivatives including, for example, Polyquaternium 10, Polyquaternium 24, and Polyquaternium 67), cationic guar derivatives, cationic methacrylamido polymers, synthetic cationic polymers (e.g., Polyquaternium 6 and Polyquaternium 7), and quaternary trialkylammonium halide compounds including, for example, dihydroxypropyl trialkyl ammonium chloride commercially available from The Down Chemical Company under the trade name PD QUAT. In certain preferred embodiments, the cationic polymer is a cationically modified hydroxyethylcellulose, which is commercially available from The Dow Chemical Company under the trade name UCARE or SOFTCAT. In certain embodiments, the hair care compositions include a cationic polymer in an amount of from 0.05 to 20 weight %, preferably from 0.1 to 20 weight %, and more preferably from 1.0 to 3.0 weight %, by weight of the composition.

In certain embodiments, the inventive hair care compositions include an emollient. Suitable emollients include, for example, hydrocarbon oils, esters, natural oils, fatty acids, or silicones. Suitable silicones and silicone oils include, for example, volatile or non-volatile polymethylsiloxanes (PDMS) comprising a linear or cyclic silicone chain (which are liquid or pasty at room temperature), preferably cyclopolydimethylsiloxanes (cyclomethicones, e.g., cyclopentasiloxane and cyclohexadimethylsiloxane), polydimethylsiloxanes comprising alkyl, alkoxy or phenyl groups (which are pendent or at the end of a silicone chain and comprise from 2 to 24 carbon atoms), phenyl silicones (e.g., phenyl trimethicones, phenyl dimethicones, phenyltrimethylsiloxydiphenylsiloxanes, diphenyl dimethicones, diphenylmethyldiphenyltrisiloxanes 2-phenylethyltrimethyl siloxysilicates, and polymethylphenylsiloxanes), fluoro oils (e.g., partially hydrocarbon-based and/or partially silicone-based fluoro oils, and combinations thereof. In certain preferred embodiments, the emollient comprises a blend of dimethicone, Laureth-23, and C 12-15 Pareth-3, which is commercially available from Dow-Corning under the trade name DOW CORNING 2-1491 Silicone Emulsion (also described as a 60% large particle size non-ionic emulsion of a blend of ultra-high molecular weight polydimethylsiloxane gum and intermediate molecular weight polydimethylsiloxane fluid). In certain embodiments, the hair care compositions include an emollient in an amount of from 0.1 to 5 weight %, preferably from 0.75 to 3 weight %, and more preferably from 1 to 2 weight %, by weight of the hair care composition.

In certain embodiments, the inventive hair care compositions include a surfactant. Suitable surfactants include, for example, cationic, anionic, or amphoteric surfactants, and combinations thereof. In certain embodiments, the surfactant is a nonionic/emulsifier surfactant. In certain embodiments, the surfactant is a cationic surfactant, preferably behentrimonium chloride. In such embodiments, the surfactant may be present in an amount of from 0.1 to 10 weight %, preferably from 0.5 to 7 weight %, and more preferably from 1 to 4 weight %, by weight of the composition. In certain embodiments, the surfactant comprises a detergent surfactant. In such embodiments, the surfactant is present in an amount of from 1 to 25 weight %, preferably from 5 to 20 weight %, and more preferably from 7 to 18 weight %, by weight of the composition. Preferably, the detergent surfactant comprises an anionic surfactant in combination with an amphoteric surfactant. Suitable anionic surfactants include, for example, ammonium laureth sulfate, ammonium lauryl sulfate, sodium laureth sulfate, sodium lauryl sulfate, and combinations thereof. In certain embodiments, the anionic surfactant is present in an amount of from 1 to 25 weight %, preferably from 5 to 20 weight %, and more preferably from 7 to 15 weight %, by weight of the composition. In certain embodiments, the mixture is an anionic surfactant in combination with a second surfactant comprising at least one of disodium cocoamphodiacetate, decylglucoside, or cocamidopropyl betaine. In certain embodiments, the second surfactant is present in an amount of from 1 to 10 weight %, preferably from 1 to 8 weight %, and more preferably from 2 to 6 weigh %, by weight of the composition. In certain preferred embodiments, the surfactant is a mixture of sodium laureth sulfate (such as is commercially available from Cognis under the trade name STANDAPOL ES) and disodium cocoamphodiacetate (such as is commercially available from Henkel under the trade name VELVETEX CDC). In certain embodiments in which the surfactant is a mixture of sodium laureth sulfate and disodium cocoamphodiacetate, the ratio of sodium laureth sulfate to disodium cocoamphodiacetate is in a range from 9:1 to 2:1, preferably about 6:1.

In certain embodiments, the inventive hair care compositions include a rheology modifier. Suitable rheology modifiers include, for example, modified or unmodified carboxyvinyl polymers (e.g., the products sold under the names CARBOPOL and PEMULEN (INCI name: Acrylates/C10-30 alkyl acrylate crosspolymer; available from Lubrizol)), polyacrylates and polymethacrylates (e.g., the products sold under the names LUBRAJEL and NORGEL (commercially available from Guardian) or HISPAGEL (commercially available from Hispano Chimica) or ACULYN rheology modifiers (commercially available from The Dow Chemical Company), polyacrylamides, 2-acrylamido-2-methylpropanesulfonic acid polymers and polymers (which are optionally crosslinked and/or neutralized (e.g., the poly(2-acrylamido-2-methylpropane-sulfonic acid) sold by Clariant (INCI name: ammonium polyacryldimethyltauramide)), emulsified crosslinked anionic polymers of acrylamide and AMPS (e.g., those sold under the name SEPIGEL 305 (INCI name: Polyacrylamide/C13-14 Isoparaffin/Laureth-7; from Seppic) and under the name SIMULGEL 600 (INCI name: Acrylamide/Sodium acryloyldimethyltaurate polymer/Isohexadecane/Polysorbate 80; from Seppic)), polysaccharide biopolymers (e.g., xanthan gum, guar gum, carob gum, acacia gum, scleroglucans, chitin and chitosan derivatives, carrageenans, gellans, alginates, celluloses (e.g., microcrystalline cellulose), cellulose derivatives, associative polymers (e.g., associative polyurethanes), polymers comprising at least two hydrocarbon-based lipophilic chains comprising from 6 to 30 carbon atoms, separated with a hydrophilic sequence (e.g., the polyurethanes sold under the names SERAD FX1010, SERAD FX1100 and SERAD FX1035 (commercially available from Hüs America), RHEOLATE 255, RHEOLATE 278 and RHEOLATE 244 (INCI name: Polyether-urea-polyurethane; from Rheox), DW 1206F, DW 1206J, DW 1206B, DW 1206G, and ACULYN 46 (commercially available from The Dow Chemical Company)). In certain embodiments, the hair care compositions include a rheology modifier in an amount of from 0.05 to 5.0 weight %, preferably from 0.1 to 3.0 weight %, and more preferably 0.5 to 2.0 weight %, by weight of the composition.

In certain embodiments, the inventive hair care compositions include a cosmetic active, e.g., an additional anti-dandruff active. Suitable additional anti-dandruff actives include, for example, octopirox (piroctone olamine), azole antimicrobials (e.g., climbazole), selenium compounds (i.e., selenium sulfide), zinc pyrithione (unaltered), salicylic acid, and combinations thereof. In certain embodiments, the hair care compositions include a cosmetic active in an amount of from 0.01 to 5 weight %, preferably from 0.1 to 3 weight %, and more preferably from 0.3 to 1 weight %.

The hair care compositions of the present invention may also include a dermatologically acceptable carrier. Such material is typically characterized as a carrier or a diluent that does not cause significant irritation to the skin and does not negate the activity and properties of active agent(s) in the composition. Examples of dermatologically acceptable carriers that are useful in the invention include, without limitation, water, such as deionized or distilled water, emulsions, such as oil-in-water or water-in-oil emulsions, alcohols, such as ethanol, isopropanol or the like, acetone, glycols, such as propylene glycol, glycerin or the like, creams, aqueous solutions, oils, ointments, pastes, gels, lotions, milks, foams, suspensions, powders, or mixtures thereof. In some embodiments, the composition contains from about 99.99 to about 50% by weight of the dermatologically acceptable carrier, based on the total weight of the composition.

In certain embodiments, the hair care composition contains other optional ingredients, including, for example, humectants, waxes, sensory modifiers, preservatives/antioxidants/chelating agents, reducing agents, pH adjusting agents/buffers/neutralizing agents, sunscreen actives, vitamins, proteins/amino acids, plant extracts, natural ingredients, bio-actives, fragrances/perfumes, foaming agents, penetrants, volatiles/propellants/solvents/carriers, liquid vehicles/solvents/carriers, salts, anti-static agents, anti-frizz agents, hair waving/straightening agents, absorbents, colorants, and hard particles. The amount of optional ingredients effective for achieving the desired property provided by such ingredients can be readily determined by one skilled in the art.

As noted above, the hair care compositions of the present invention are highly effective as anti-dandruff additives for impeding dandruff on hair because of the enhanced deposition of the zinc salt included in the composition. They exhibit anti-dandruff attributes on par with, if not better than, previously known additives for hair care applications, without the disadvantage of disrupting the desirable visual appearance (e.g., a pearlescent effect) of the composition or contributing to poor smoothness/sensory feel after deposition onto hair. Accordingly, the hair care compositions of the present invention are useful for the treatment of dandruff in hair. Thus, in one aspect the present invention provides that the hair care compositions may be used in a method for reducing dandruff comprising applying to the scalp a hair care composition comprising the zinc salt coated polyurethane microparticles described herein and at least one cosmetically acceptable cationic polymer, emollient, surfactant, rheology modifier, or cosmetic active.

In practicing the methods of the invention, the hair care compositions are generally administered topically by applying the compositions onto the hair. A person of ordinary skill in the art can readily determine the frequency with which the compositions should be applied. The frequency may depend, for example, on the amount of dandruff that an individual is encountering in a given day and/or the sensitivity of the individual to dandruff. By way of non-limiting example, administration on a frequency of at least once per day may be desirable.

Some embodiments of the invention will now be described in detail in the following Examples.

EXAMPLES

Example 1

Preparation of Exemplary Zinc Pyrithione Coated Polyurethane Microparticles

Exemplary zinc pyrithione coated polyurethane microparticles of the present invention were prepared in three phases: pre-polymer preparation; preparation of the polyurethane microsphere suspension; and coating of the polyurethane microparticle with zinc pyrithione via spray drying.

Pre-Polymer Preparation 120 g of PTMEG 2000 (poly(tetramethylene ether)glycol) from Sigma-Aldrich was heated at 120° C. for 1 hour and then cooled to 50° C. The pre-polymer stock solution was obtained by adding 45 g of IPDI (isophorone diisocyanate) from Sigma-Aldrich to the PTMEG solution and heating at 94° C. for 3.5 hours. The system was purged under $N_2$ throughout the reaction process. The NCO value of the pre-polymer stock solution was 2 to 8 weight % as measured by titration.

Preparation of Polyurethane Microparticle Suspension 60 g of the pre-polymer solution was added to 240 g of PVA 2088 (polyvinyl alcohol) available from Sigma-Aldrich in 7 weight % solution at 4° C. dropwise under high speed stirring at 2,000 rpm. The solution was stirred for an additional 30 minutes after addition of the pre-polymer solution to the PVA. DETA aqueous (25 weight %, 1.1× molar ratio to NCO groups in pre-polymer solution) was introduced into the suspension and continuously stirred for 40 minutes. The obtained suspension was washed and centrifuged to collect a polyurethane slurry. FIG. 1 demonstrates via IR spectroscopy that no residual —NCO was found in the polyurethane particles.

Coating of the Polyurethane Microparticle with Zinc Pyrithione

A zinc pyrithione (ZPT) suspension (Zinc Omadine FPS; 48% aqueous dispersion) available from Arch Personal Care Products was mixed with the polyurethane (PU) slurry in three different weight ratios of zinc pyrithione suspension to polyurethane slurry: 0.5:9.5; 1.0:9.0; and 2.0:8.0. Each mixture was then diluted with water to create a 50× diluted composite particle dilution. Each dilution was then spray dried (air inlet temp: 110° C.; air speed: 40; flow rate: 10 ml/min) to obtain the zinc pyrithione coated polyurethane microparticles (ZPU).

Example 2

Particle Morphology Evaluation

The particle morphology of polyurethane particles (from the polyurethane slurry) and the three batches of zinc pyrithione coated polyurethane particles as prepared in Example 1 above was evaluated by scanning electron microscopy (SEM) using an FEI Nova™ Nano SEM630. The size distribution of each sample is reported below in Table 1.

TABLE 1

Size Distribution of Polyurethane Microparticles

| Sample | Size Distribution |
| --- | --- |
| Polyurethane (unaltered) | 1-20 microns |
| ZPU (0.5:9.5) | 1-20 microns |
| ZPU (1.0:9.0) | 1-20 microns |
| ZPU (2.0:8.0) | 1-20 microns |

Example 3

Surface Analysis of Zinc Pyrithione Coated Polyurethane Microparticles

Figure 2:
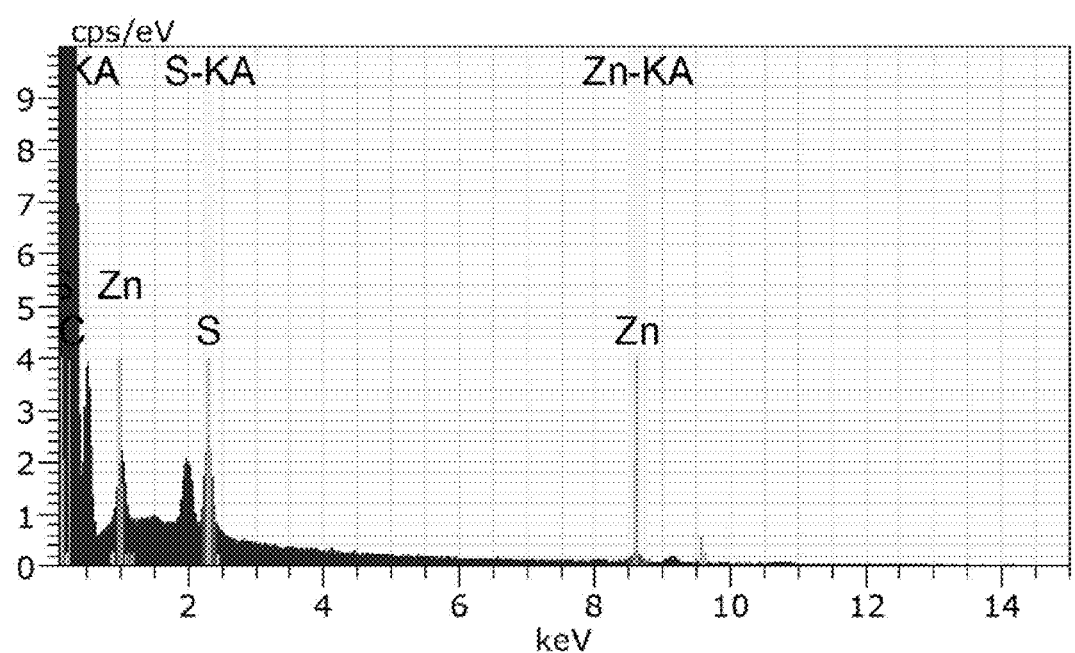
FIG. 2 shows an energy-dispersive X-ray spectrum of zinc pyrithione coated polyurethane microparticles having a zinc pyrithione to polyurethane weight ratio of 1.0:9.0.

The composition of the surface of ZPU (1.0:9.0) particles as prepared in Example 1 above was analyzed via energy-dispersive X-ray spectroscopy (EDX). The EDX elemental analysis shown in FIG. 2 demonstrates that Zn and S elemental peaks were observed from the particles. Color highlighted elements signal by mapping technology indicated that the elemental response came from the surface of the microparticle, confirming that the ZPU particles prepared substantially in accordance with Example 1 were hybrid microparticles of PU coated with ZPT.

Example 4

Preparation of Hair Care Shampoo Compositions

Exemplary hair care shampoos of the present invention contain the components recited below in Table 2.

TABLE 2

Hair Care Compositions

| Component | C1 (wt %) | C2 (wt %) | C3 (wt %) | C4 (wt %) | E1 (wt %) |
|---|---|---|---|---|---|
| Base Shampoo+ | 98.0 | 98.0 | 98.0 | 98.0 | 98.0 |
| Deionized Water | 2.0 | 1.8 | — | 1.0 | — |
| Polyurethane (PU) | — | — | 1.8 | — | — |
| Zinc Pyrithione (ZPT) | — | 0.2 | 0.2 | 1.0 | — |
| Zinc Pyrithione Coated Polyurethane (ZPU; ZPT:PU = 1:9) | — | — | — | — | 2.0 |

+The pearlescent base shampoo is available from LUX under the trade name Moisture & Silk; labeled ingredients are: Water, Sodium Lauryl ether sulfate, Coco-amidopropyl betaine, Ethylene glycol distearate, Dimethiconol, Amino dimethylsilicones, Amino acids, Acrylate Co-polymer, Coconut oil monoethanol-amine, Guar gum_2 hydroxy-3-(trimethylammonium)propyl ether chloride, NaCl, Citric acid, EDTA, preservatives.
ZPT particles, PU particles, and ZPU particles were added to each respective base shampoo formulation and stirred at 350 rpm for 20 minutes.

Example 5

Evaluation of Pearlescent Effect/Visual Appearance

The effect on the visual appearance of shampoos containing inventive ZPU particles as prepared in Examples 1 and 4 above was evaluated. Each of the four hair care formulations prepared in Example 4 was sealed in a glass vial and scanned using a Npheloskan Spectrometer. Pixel variance enhancement technology was utilized to demonstrate the pearlescent effect of the samples as reported below in Table 3.

TABLE 3

Pixel Variance Enhancement Value of Pearlescent Effect

| Sample | Pixel Variance Enhancement (PVE) Value | Relative Pearlescent Intensity (vs Base Shampoo) |
|---|---|---|
| C1 (Base Shampoo (pearlescent)) | 53.2 | 100% |
| C2 (Base Shampoo + 0.2% ZPT) | 19.5 | 36.6% |
| C3 (Base Shampoo + 0.2% ZPT + 1.8% PU) | 19.0 | 35.7% |
| E1 (Base Shampoo + 2% ZPU (ZPT:PU = 1:9)) | 38.0 | 71.4% |

As shown in Table 3, inventive samples containing 2% ZPU demonstrated very good relative pearlescent intensity, which can be observed by the naked eye. The pearlescent effect was greatly reduced for the samples containing 0.2% ZPT. These results demonstrate that the inventive hair care compositions containing zinc pyrithione coated polyurethane microparticles provide superior retention of pearlescent effect when added to a base shampoo as compared to base shampoos containing (unaltered) zinc pyrithione with or without (unaltered) polyurethane microparticles.

Example 6

Tactile Smoothness Measurements

Figure 3:
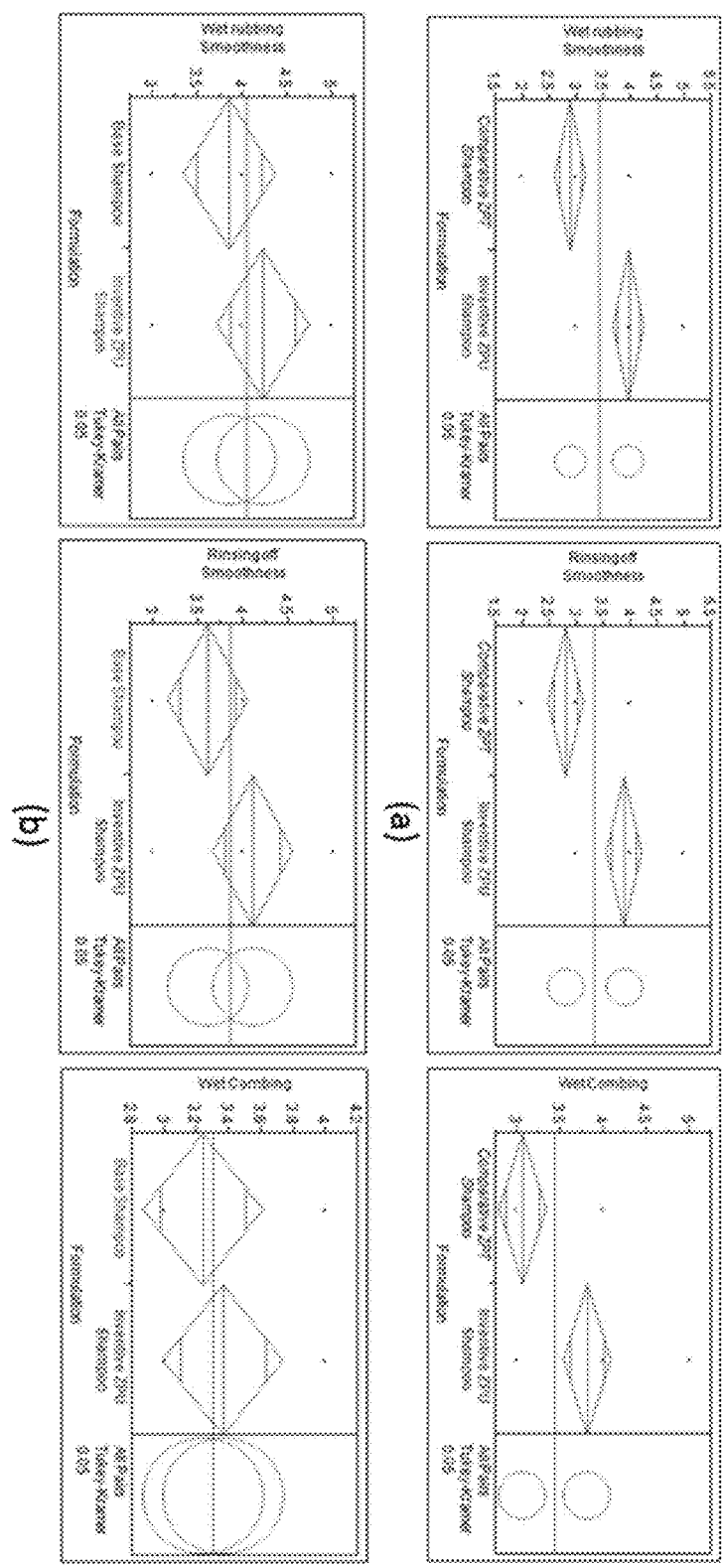
FIG. 3 shows the sensory performance (i.e., wet rubbing smoothness, rinsing off smoothness, and wet combing) of hair treated with (a) a shampoo containing zinc pyrithione compared against the inventive shampoo containing zinc pyrithione coated polyurethane microparticles, and (b) a comparative base shampoo compared against the inventive shampoo containing zinc pyrithione coated polyurethane microparticles.

Samples C1 (base shampoo), C4 (base shampoo+1% ZPT), and E1 (base shampoo+2% ZPU) as prepared in Example 4 above were evaluated for tactile smoothness of hair (a) during application to hair after wetting with water at 40° C. ("Wet-Rubbing Test"), (b) after rinsing of the shampoo composition for 30 seconds with water at 40° C. ("Rinsing-Off Test"), and (c) ease of combing of wet hair after rinsing ("Wet Combing Test"). The hair was evaluated by a panel of 12 persons for each test on a scale of 1 (indicating poor smoothness) to 5 (indicating good smoothness). FIG. 3(a) shows that the inventive zinc pyrithione coated polyurethane microparticle shampoo compositions performed dramatically better than the comparative zinc pyrithione (unaltered) shampoo compositions in all three tests. FIG. 3(b) demonstrates that the inventive zinc pyrithione coated polyurethane microparticle shampoo compositions performed favorably when compared against the base shampoo in all three tests.

What is claimed is:

1. A composition comprising polyurethane microparticles coated with zinc salt particles, wherein the ratio of zinc salt to polyurethane is in a range of from 1:99 to 3:7, and the polyurethane microparticles have an average particle size of less than 100 microns, wherein the zinc salt comprises zinc pyrithione having an average particle size of less than 2 microns.

2. The composition of claim 1, wherein the composition is a hair care composition further comprising at least one cosmetically acceptable cationic polymer, emollient, surfactant, rheology modifier, or cosmetic active.

3. The composition of claim 1, wherein the polyurethane microparticles have an average particle size of less than 30 microns.

4. The composition of claim 1, wherein the zinc pyrithione particles have an average particle size of less than 1 micron.

5. The composition of claim 1, wherein the ratio of zinc pyrithione to polyurethane is in a range of from 0.5:9.5 to 3:7.

6. The composition of claim 1, wherein the ratio of zinc pyrithione to polyurethane is in a range of from 1.0:9.0 to 2.0:8.0.

* * * * *